(12) United States Patent
Hirabara et al.

(10) Patent No.: US 8,920,328 B2
(45) Date of Patent: Dec. 30, 2014

(54) BLOOD PRESSURE MEASUREMENT APPARATUS

(75) Inventors: Hideaki Hirabara, Tokyo (JP); Mitsushi Hyogo, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 1137 days.

(21) Appl. No.: 12/323,509

(22) Filed: Nov. 26, 2008

(65) Prior Publication Data

US 2009/0137912 A1    May 28, 2009

(30) Foreign Application Priority Data

Nov. 28, 2007   (JP) ................... 2007-306903

(51) Int. Cl.
*A61B 5/02* (2006.01)
*A61B 5/022* (2006.01)
*A61B 5/024* (2006.01)

(52) U.S. Cl.
CPC ............. *A61B 5/022* (2013.01); *A61B 5/02225* (2013.01); *A61B 5/024* (2013.01)
USPC ........................................................ 600/485

(58) Field of Classification Search
None
See application file for complete search history.

(56) References Cited

U.S. PATENT DOCUMENTS

| 5,931,790 | A | * | 8/1999 | Peel, III .................... | 600/494 |
| 6,152,881 | A | | 11/2000 | Raines et al. | |
| 2003/0065270 | A1 | * | 4/2003 | Raines et al. ................. | 600/504 |

FOREIGN PATENT DOCUMENTS

| JP | 63-3835 A | 1/1988 |
| JP | H06-47009 A | 2/1994 |
| JP | 2002-112972 A | 4/2002 |
| JP | 2002-539879 A | 11/2002 |
| JP | 2003-144399 A | 5/2003 |

OTHER PUBLICATIONS

Japanese Office Action for related Japanese Application No. 2007-306903 dated Dec. 20, 2011.

* cited by examiner

*Primary Examiner* — Chris L Chin
*Assistant Examiner* — Richard Moerschell
(74) *Attorney, Agent, or Firm* — Kenealy Vaidya LLP

(57) ABSTRACT

A blood pressure measurement apparatus includes: a detector, operable to detect a first pulse, a second pulse prior to the first pulse and a third pulse prior to the second pulse under the same pressure; a first distinguisher, operable to distinguish whether waveforms of the first and second pulses are substantially identical with each other; a second distinguisher, when the waveforms are not substantially identical with each other, operable to distinguish whether parameters of the first, second and third pulses meet a condition corresponding to arrhythmia; a determiner, operable to determine the first and second pulses to be pulse waves when the waveforms are substantially identical with each other, and operable to determine the first, second and third pulses to be pulse waves when the parameters meet the condition; and a calculator, operable to calculate a blood pressure value based on the pulse waves.

3 Claims, 4 Drawing Sheets

BLOOD PRESSURE MEASUREMENT APPARATUS

BACKGROUND OF THE INVENTION

The present invention relates to an oscillometric blood pressure measurement apparatus, taking in pressure pulses from a signal corresponding to a pressure of a cuff and calculating a blood pressure based on this signal.

With this type of blood pressure measurement apparatus, a cuff is wound around an upper arm of a subject, pressure pulses are taken in continuously from a signal corresponding to a cuff pressure in a state where the cuff pressure is maintained at a prescribed value, and, when two pressure pulses of a substantially same waveform occurs continuously, recognizing the pressure pulses as pressure pulses that can be used for blood pressure calculation, and thereafter decreasing the cuff pressure in micro steps and measuring pressure pulses in likewise manner. These measurements are performed until calculation of the blood pressure is enabled. Here, there is a problem when arrhythmia occurs and an amplitude of a pressure pulse and a pulse rate change due to an extrasystole, etc. In this case, two continuous pressure pulses are not acquired and because measurements are made repeatedly while maintaining the cuff pressure until the pulses are acquired, much time is required for measurement. These circumstances are described, for example, in paragraph 0006 and FIG. 2 in JP-A-2002-112972.

To solve the above issue, in JP-A-2002-112972, a sensor (ECG sensor), detecting presence of arrhythmia, is used, detection is performed using a first pulsation complex criterion when arrhythmia is not detected, and detection is performed using a second pulsation complex criterion that is more lax than the first pulsation complex criterion to compensate for presence of arrhythmia when arrhythmia is detected.

In JP-A-2003-144399, by a cuff pulse wave amplitude correcting unit, correcting a cuff pulse wave amplitude, an amplitude of each cuff pulse wave is corrected based on a nonlinear relationship between a pressure difference, which is a difference between a cuff pressure and a mean blood pressure of a living body, and the cuff pulse wave amplitude, and because a blood pressure value of the living body is determined based on a change of the corrected cuff pulse wave amplitude, even when arrhythmia occurs, an accurate envelope is determined to enable blood pressure measurement to be performed or blood pressure measurement to be performed at high precision.

The apparatus described in JP-A-2002-112972 requires a sensor specialized to detect the presence of arrhythmia and this leads to making the configuration complex and large. The apparatus described in JP-A-2003-144399 requires a photoplethysmograph as the cuff pulse wave amplitude correcting unit and this also leads to making the configuration complex and large.

SUMMARY

It is therefore an object of the invention to provide a blood pressure measurement apparatus with a simple configuration enabling highly precise blood pressure measurements to be made without requiring much time even when arrhythmia occurs.

In order to achieve the object, according to the invention, there is provided a blood pressure measurement apparatus, operable to vary a pressure of a cuff wound around a portion of a living body to calculate a blood pressure value, the blood pressure measurement apparatus comprising:

a pressure pulse detectors, operable to continuously detect pressure pulses from a signal corresponding to the pressure of the cuff, the pressure pulses including a first pulse, a second pulse prior to the first pulse and a third pulse prior to the second pulse which are detected under the same pressure;

a first distinguisher, operable to distinguish whether or not waveforms of the first pulse and the second pulse are substantially identical with each other;

a second distinguisher, when the waveforms are not substantially identical with each other, operable to distinguish whether or not parameters of the first pulse, the second pulse and the third pulse meet a condition corresponding to arrhythmia;

a determiner, operable to determine the first pulse and the second pulse to be pulse waves when the waveforms are substantially identical with each other, and operable to determine the first pulse, the second pulse and the third pulse to be pulse waves when the parameters meet the condition; and a calculator, operable to calculate the blood pressure value based on the pulse waves determined by the determiner.

The parameter may include: an amplitude of the first pulse which is expressed as A1, an amplitude of the second pulse which is expressed as A2 and an amplitude of the third pulse which is expressed as A3; and an interval between the first pulse and the second pulse which is expressed as T12 and an interval between the second pulse and the third pulse which is expressed as T23. The condition may be a first condition including: the A1 is larger than the A2; the A2 is smaller than the A3; and the T12 is longer than the T23, or a second condition including; the A1 is smaller than the A2, the A2 is larger than the A3 and the T12 is shorter than the T23.

The parameter may further include: a magnitude of a peak value of the first pulse with respect to a criterial value which is expressed as P1; a magnitude of a peak value of the second pulse with respect to the criterial value which is expressed as P2; and a magnitude of a peak value of the third pulse with respect to the criterial value which is expressed as P3. The first condition may further include the P1 is larger than the P2 and the P2 is smaller then the P3, and the second condition may further include the P1 is smaller than the P2 and the P2 is larger than the P3.

DETAILED DESCRIPTION OF PREFERRED EMBODIMENTS

With the present invention, pulse waves, which are not used in blood pressure calculation based on such physiology as described below in case of extrasystole and other forms of arrhythmia, are enabled to be used in the related-art blood pressure calculation. That is, because heart rate due to extrasystole (extrasystolic beat) is short in interval from an immediately prior normal heart rate, a blood reserving period in a ventricle is short and the heartbeat thus becomes small. In such a case where the extrasystolic beat occurs as premature beat, because a long resting phase follows and continues to a subsequent normal heart beat, the normal heart beat appearing subsequent the premature systolic beat becomes a large heartbeat. Here, such pulse waves are enabled to be used in blood pressure calculation when the pulse waves are detected.

Figure 1:
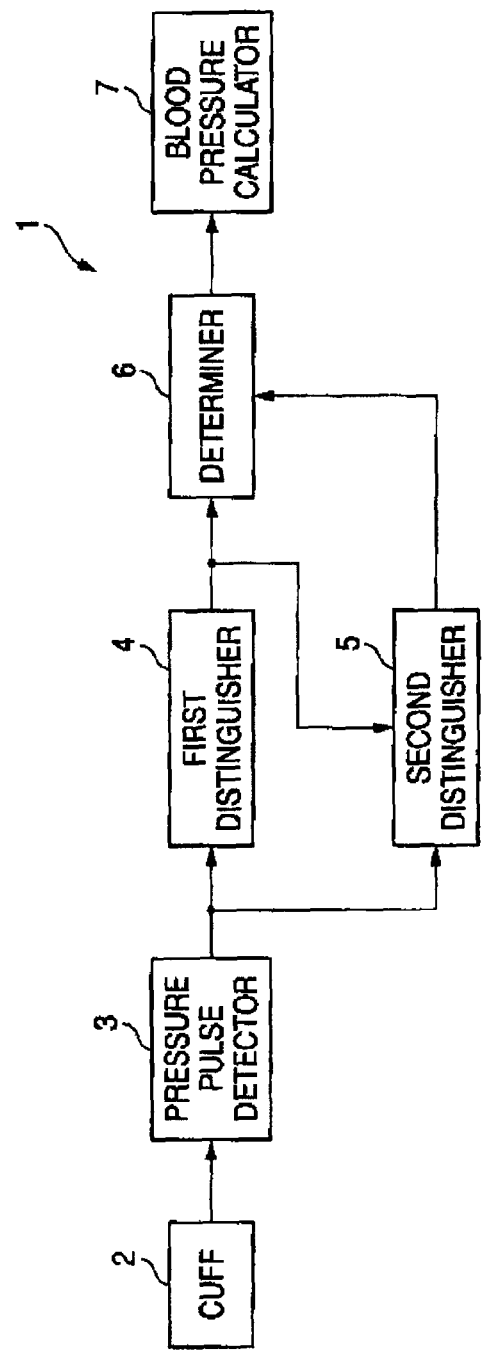
FIG. 1 is a functional block diagram of a blood pressure monitoring apparatus according to an embodiment of the present invention.

FIG. 1 is a functional block diagram of a blood pressure measurement apparatus according to the present invention. With the blood pressure measurement apparatus 1, a pressure of a cuff 2, wound around an upper arm, etc., of a subject is varied stepwise in micro steps, pulse waves synchronized to heart rate are detected under each pressure, and the blood pressure value is calculated based on the pulse waves.

Pressure pulses of no less than a prescribed threshold value from the pressure of the cuff 2 are detected continuously by a pressure pulse detector 3, waveforms of a most recent pressure pulse (first pulse), detected by the pressure pulse detector 3, and a pressure pulse (second pulse), detected immediately before the first pressure pulse under the same cuff pressure as that of the first pulse, are compared and whether or not the waveforms of the first pulse and the second pulse are substantially identical with each other is distinguished by a first distinguisher 4. As distinguishing parameters, a gradient of rise (A/T) of a pulse may be used in addition to an amplitude (A) and a rise time (t). More accurate distinction is thereby enabled.

Figure 2:
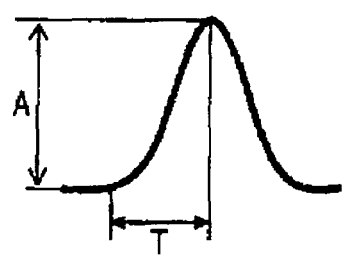
FIG. 2 is a waveform diagram for describing criteria for pulse wave detection performed by the blood pressure monitoring apparatus according to the embodiment of the present invention.

A waveform of a pressure pulse that is compared by the first distinguisher 4 is shown in FIG. 2. The distinction of whether or not the waveforms of the first pulse and the second pulse are substantially identical with each other is made by comparing the amplitudes A and the pulse rise times T of the pulses. For example, when respective differences are within 10%, both pulses are deemed to be substantially identical with each other.

If the waveforms of the first pulse and the second pulse are not distinguished to be substantially identical with each other by the first distinguisher 4, whether or not parameters of a pressure pulse (third pulse), detected immediately before the second pulse under the same cuff pressure as that of the first pulse and the second pulse, the second pulse, and the first pulse meet a condition corresponding to arrhythmia is distinguished by a second distinguisher 5. In this case, whether or not the first to third pulses can be used in blood pressure calculation based on the physiology in case of the above-described arrhythmia is distinguished.

Amplitudes of the first pulse, the second pulse, and the third pulse and intervals between adjacent two of the pulses are used as the parameters, with A1, A2, and A3 being the amplitudes of the first pulse, the second pulse, and the third pulse, respectively, T12 being the interval between the first pulse and the second pulse, and T23 being the interval between the second pulse and the third pulse.

According to the above-described physiology, the following are conditions that can be assumed to be due to arrhythmia. That is the conditions are the two cases of; A1>A2, A2<A3 and T12>T23 (first condition); and A1<A2, A2>A3 and T12<T23 (second condition).

Figure 3:
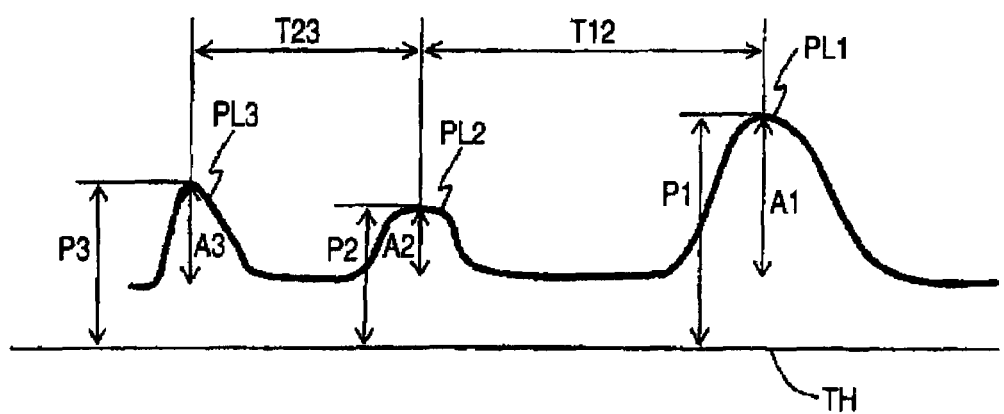
FIG. 3 is a waveform diagram for describing a first condition for arrhythmia used in the blood pressure monitoring apparatus according to the embodiment of the present invention.

FIG. 3 shows waveforms meeting the first condition, and the waveforms of the respectively adjacent pressure pulses are not distinguished as being substantially identical with each other by the first distinguisher. In the figure, the waveform at the right side indicates a most recently detected first pulse PL1, the central waveform indicates a second pulse PL2, detected immediately before the first pulse PL1, and the waveform at the left side indicates a third pulse PL3, detected immediately before the second pulse PL2. In this case, although the second pulse PL2 is an extrasystolic beat and is a pressure pulse that is not used in the related-art blood pressure calculation, it is distinguished as being a pulse wave that can be used for blood pressure calculation in the present invention.

With the present invention, magnitudes of respective peak values of the first pulse, the second pulse, and the third pulse with respect to a prescribed criterial value may be added to the parameters. In FIG. 3, a symbol TH indicates the prescribed criterial value, which, for example, is 0 volts. When P1 is the magnitude with respect to the reference value of the peak value of the first pulse PL1, P2 is the magnitude of the peak value of the second pulse PL2, and P3 is the magnitude of the peak value of the third pulse PL3, the condition includes P3>P2 and P2<P1 in addition to the first condition.

Figure 4:
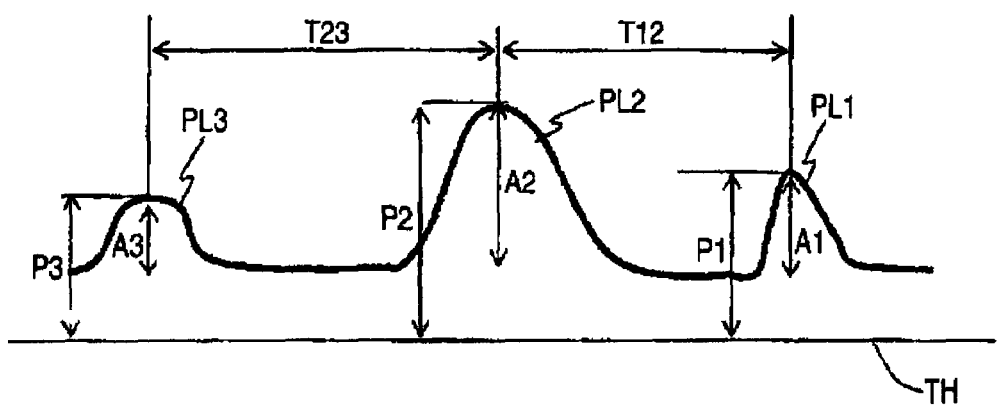
FIG. 4 is a waveform diagram for describing a second condition for arrhythmia used in the blood pressure monitoring apparatus according to the embodiment of the present invention.

FIG. 4 shows waveforms meeting the second condition, and the waveforms of the respectively adjacent pressure pulses are not distinguished as being substantially identical with each other by the first distinguisher. In the figure, the waveform at the right side indicates the most recently detected first pulse PL1, the central waveform indicates the second pulse PL2, detected immediately before the first pulse PL1, and the waveform at the left side indicates the third pulse PL3, detected immediately before the second pulse PL2. In this case, although the third pulse PL3 is an extrasystolic pulse and is a pressure pulse that is not used in the related-art blood pressure calculation, it is distinguished as being a pulse wave that can be used for blood pressure calculation in the present invention.

The magnitudes of respective peak values of the first pulse, the second pulse, and the third pulse with respect to the prescribed criterial value may be added to the parameters. In FIG. 4, the symbol TH is the prescribed criterial value, which, for example, is 0 volts. When P1 is the magnitude with respect to the prescribed criterial value of the peak value of the first pulse PL1, P2 is the magnitude of the peak value of the second pulse PL2, and P3 is the magnitude of the peak value of the third pulse PL3, the condition includes P3<P2 and P2>P1 in addition to the second condition.

A symbol 6 indicates a determiner, which, when the first distinguisher 4 distinguishes the waveforms of the first pulse and the second pulse to be substantially identical with each other or when the second distinguisher 5 distinguishes the parameters of the first pulse, the second pulse, and the third pulse as meeting the condition, determines the respective pressure pulses as the pulse waves to be used in blood pressure calculation and calculates and determines an amplitude of the pulse waves at the cuff pressure. The amplitude of the pulse waves is determined as follows.

When the first distinguisher 4 distinguishes the waveforms of the first pulse and the second pulse to be substantially identical with each other, the amplitude of the pulse waves is an average value of the amplitudes of the first pulse and the second pulse.

When the second distinguisher 5 distinguishes the parameters of the first pulse, the second pulse, and the third pulse as meeting either the first condition or the second condition, the amplitude of the pulse waves is an average value of the amplitudes of the first pulse, the second pulse, and the third pulse.

Based on the amplitude of the pulse waves thus determined by the determiner 6, a mean blood pressure, a systolic blood pressure, and a diastolic blood pressure are calculated by a blood pressure calculator 7.

Embodiment 1

Figure 5:
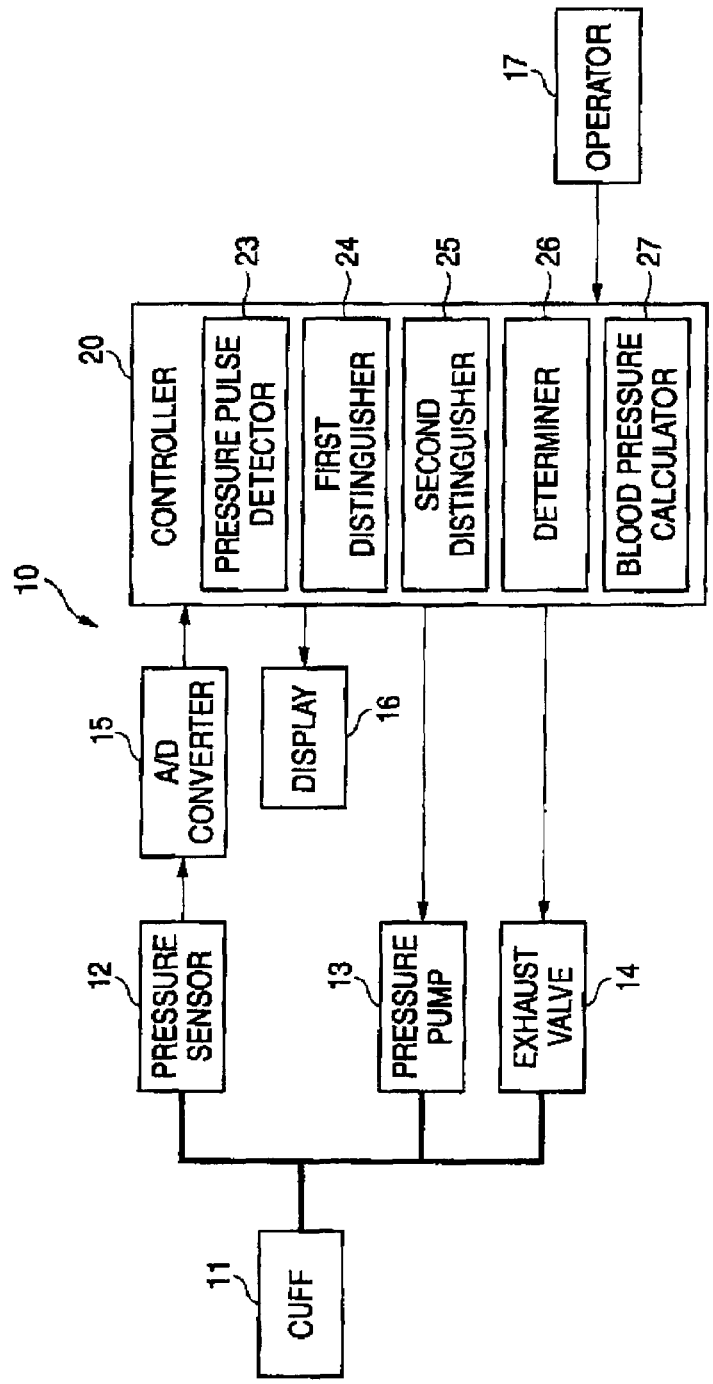
FIG. 5 is a block diagram of a configuration of a blood pressure monitoring apparatus according to an embodiment of the present invention.

Embodiments of a blood pressure measurement apparatus according to the present invention shall now be described with prescribed criterial to the figures that follow. In each figure, components that are the same shall be provided with the same symbol and redundant description shall be omitted. FIG. 5 is a configuration diagram of an embodiment of the blood pressure measurement apparatus 10 according to the present invention and here, the functions shown in FIG. 1 are realized using a central processing unit (CPU). The blood pressure measurement apparatus 10 includes a cuff 11, attached to an arm, etc., of a subject, and a pressure sensor 12, a pressure pump 13, and an exhaust valve 14 are connected to the cuff 11.

The blood pressure measuring device 10 performs a process based on control by a controller 20, including the CPU, a inflating instruction signal and a deflating instruction signal are transmitted from the controller 20 to the pressure pump 13, and instruction signals related to opening and closing of a valve that exhausts air inside the cuff 11 are transmitted from the controller 20 to the exhaust valve 14. By this configuration, the controller 20 performs stepwise control of a pressure of cuff 11 in micro steps, detects pulse waves synchronized to heart rate under the respective cuff pressures, and calculates the blood pressure based on the pulse waves.

An A/D converter 15 is disposed between the controller 20 and the pressure sensor 12, and an output of the pressure sensor 12 is digitized at a required sampling rate by the A/D converter 15 and transmitted to the controller 20. By obtaining a digital output of the A/D converter 15, the controller 20 takes in the signal (digital) corresponding to the pressure of the cuff 11, and the CPU performs processes of the respective units described below in regard to pulses in the signal.

That is, the controller 20 includes a pressure pulse detector 23, a first distinguisher 24, a second distinguisher 25, a determiner 26, and a blood pressure calculator 27, corresponding to the respective units of FIG. 1, and the CPU executes the functions of the respective units.

In the comparison of the waveforms of the two pulses by the first distinguisher 24, just one of either an amplitude A or a rise time T may be compared as a parameter, or a gradient of rise (A/T) of a pulse may be taken into consideration as well. The waveforms of the two pulses can be compared more rigorously, the larger the number of parameters considered. The abovementioned difference may be differed according to each parameter.

For example as described in JP-A-6-47009, the blood pressure calculator 27 lines up the pulse waves determined by the determiner 26 according to cuff pressure, and performs blood pressure calculation with a mean blood pressure being the corresponding cuff pressure, at which a maximum value of the amplitude is obtained, a systolic blood pressure being the cuff pressure, at which an amplitude value of ½ of the maximum value is obtained and which is higher than the mean blood pressure, and a diastolic blood pressure being the cuff pressure, at which an amplitude value of ½ of the maximum value is obtained and which is lower than the mean blood pressure.

A display 16 for displaying information is connected to the controller 20, including the CPU that realizes the respective units described above, and the blood pressure, etc., is displayed on the display 16 by control by the controller 20. An operator 17, provided with a start switch, etc., is also connected to the controller 20, and information of the operator 17 is taken into the controller 20.

Figure 6:
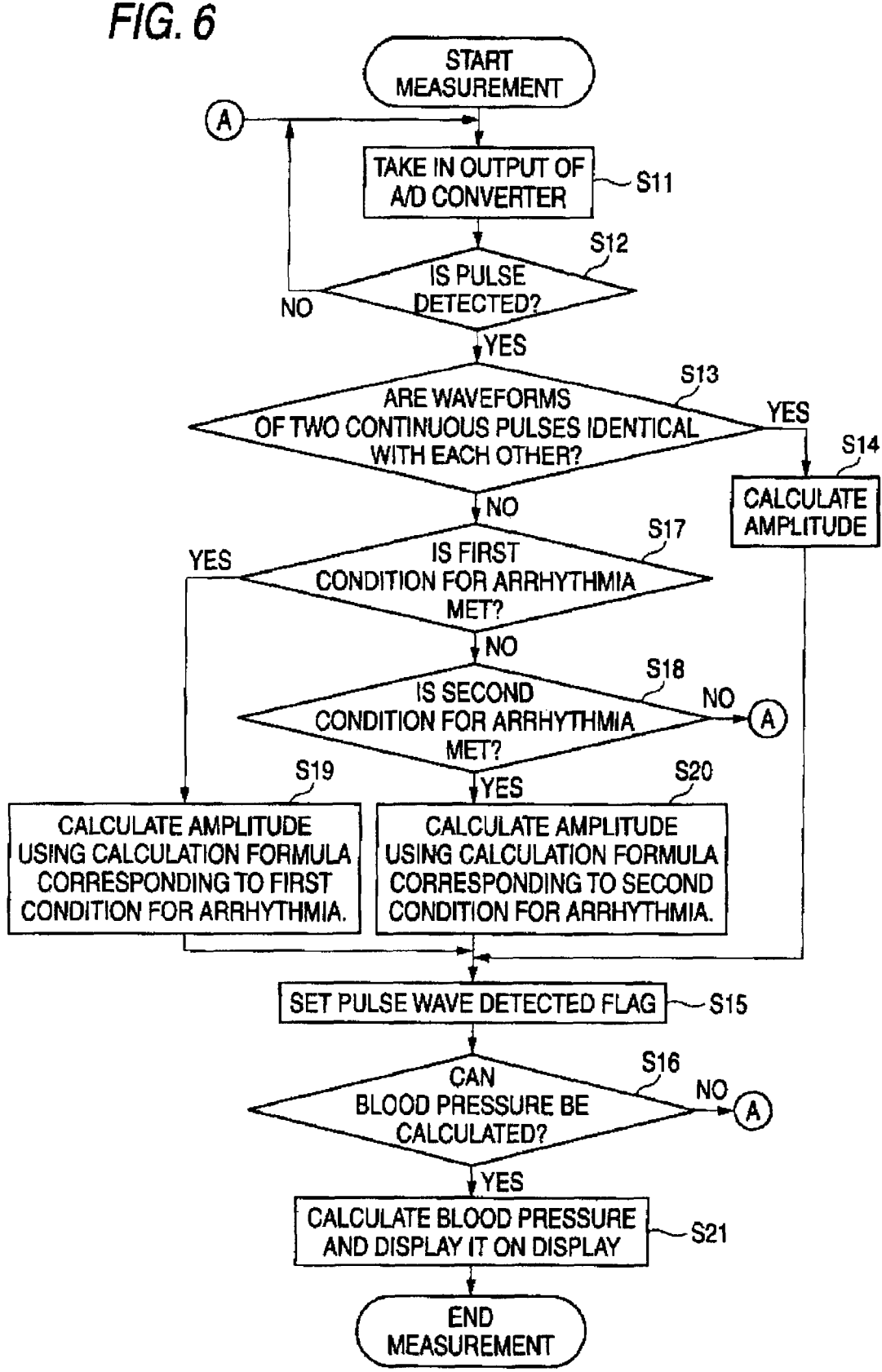
FIG. 6 is a flowchart for describing an operation of the blood pressure monitoring apparatus according to the embodiment of the present invention.

With the blood pressure monitoring apparatus configured as described above, because the respective units are realized by the CPU executing a blood pressure detecting program, corresponding to a flowchart shown in FIG. 6, an operation of the blood pressure measurement apparatus according to the present invention shall now be described according to this flowchart. When the start switch on the operator 17 is operated, an unillustrated cuff pressure control program is started, and the controller 20 controls the pressure pump 13 to supply air to the cuff 11 until a suitable cuff pressure is attained, and when the cuff pressure is attained, stops the pressure pump 13 and controls the exhaust valve 14 to perform stepwise exhaust in micro steps. In parallel, the blood pressure detecting program is started and, as shown in FIG. 6, the output of the A/D converter 15 is taken in (S11) and pressure pulse detection is performed (S12).

When a pressure pulse is detected in step S12, the waveforms of this pressure pulse and the pressure pulse, detected immediately before under the same cuff pressure, are compared, and whether or not the waveforms of the two continuous pressure pulses are substantially identical with each other is distinguished (S13). As described using FIG. 2, the distinction of whether or not the waveforms of the two pressure pulses are substantially identical with each other is made by comparing the amplitudes A and the rise times T of the respective pulses.

If in step S13, it is distinguished that the waveforms of the two continuous pressure pulses are substantially identical with each other, in step S14, the two continuous pressure pulses are deemed to be pulse waves that can be used for blood pressure calculation, and as described for the determiner 6 of FIG. 1, the average amplitude of the two pressure pulses is calculated and determined as the amplitude of the pulse waves at the cuff pressure, and then in step S15, a pulse wave detected flag, indicating that pulse waves that can be used in blood pressure calculation were detected under the cuff pressure, is set. In response to the pulse wave detected flag, the cuff pressure control program controls the exhaust valve 14 to lower the cuff pressure by a micro step and then resets the pulse wave detected flag.

Then in step S16, it is distinguished whether or not the blood pressure can be calculated. A distinction criterion in step S16 is, for example, that the blood pressure can be calculated when the amplitude of the pulse waves is less than ½ the maximum amplitude. If the blood pressure calculation criterion is not met in step S16, step S11 is returned to and the process is continued again.

If in step S13 it is not distinguished that the waveforms of the two continuous pressure pulses are substantially identical with each other, it is distinguished in step S17 whether or not three continuous pulses meet the first condition for arrhythmia, described with FIG. 3. If in step S17, it is distinguished that the first condition for arrhythmia is not met, it is distinguished in step S18 whether or not the three continuous pulses meet the second condition for arrhythmia, described with FIG. 4. If in step S18, it is distinguished that the second condition for arrhythmia is not met, step S11 is returned to and the process is continued again.

On the other hand, if in step S17, it is distinguished that the first condition for arrhythmia is met, then in step S19, the three continuous pressure pulses are deemed to be pulse waves that can be used for blood pressure calculation, and as described for the determiner 6 of FIG. 1, the average amplitude of the three pressure pulses is calculated and determined as the amplitude of the pulse waves at the cuff pressure, and then step S15 is entered. Also, if in step S18, it is distinguished that the second condition for arrhythmia is met, then in step S20, the three continuous pressure pulses are deemed to be pulse waves that can be used for blood pressure calculation, and as described for the determiner 6 of FIG. 1, the average amplitude of the three pressure pulses is calculated and determined as the amplitude of the pulse waves at the cuff pressure, and then step S15 is entered.

When upon repeating the above process, it is distinguished in step S16 that the blood pressure can be calculated, the blood pressure is calculated in step S21 using the amplitudes of the pulse waves determined in step S14, step S19, and step S20 and this is displayed on the display 16.

Thus with the blood pressure measurement apparatus according to the present invention, because pressure pulses during arrhythmia, which are not processed as pulse waves that can be used for the related-art blood pressure calculation, are taken in as pulse waves that can be used for blood pressure calculation when a condition corresponding to arrhythmia is met and blood pressure calculation is performed accordingly, a time required for blood pressure measurement in a case of arrhythmia can be shortened in comparison to the related arts.

With the blood pressure measurement apparatus according to the present invention, because when it is not distinguished that the waveforms of the first pulse and the second pulse, detected immediately before the first pulse under the same cuff pressure as the first pulse, are substantially identical with each other, the parameters of the pressure pulse (third pulse), detected immediately before the second pulse under the same cuff pressure as that of the first pulse and the second pulse, the second pulse, and the first pulse are compared to distinguish whether or not the parameters meet the condition corresponding to arrhythmia, and the first pulse, the second pulse, and the third pulse are deemed to be the pulse waves to be used in blood pressure calculation when it is distinguished that the parameters of the first pulse, the second pulse, and the third pulse meet the condition, pressure pulses meeting the condition corresponding to arrhythmia, which are not used in the related-art blood pressure calculation, can be used in blood pressure calculation, and thus by a simple configuration that does not require separate provision of a special sensor, an improvement can be made in regard to much time being required for measurement due to occurrence of arrhythmia.

Also with the present invention, because the parameters are the amplitudes of the first pulse, the second pulse, and the third pulse and the intervals between adjacent pulses, and when the amplitudes of the first pulse, the second pulse, and the third pulse are A1, A2, and A3, the interval between the first pulse and the second pulse is T12, and the interval between the second pulse and the third pulse is T23, the condition is A1>A2 and A2<A3 and T12>T23 (first condition) or is A1<A2 and A2>A3 and T12<T23 (second condition), the pressure pulses, meeting the first condition or the second condition in regard to the amplitudes and the intervals of the pressure pulses, are handled as the pulse waves that can be used for blood pressure calculation and thus by a simple configuration that does not require separate provision of a special sensor, an improvement can be made in regard to much time being required for measurement due to occurrence of arrhythmia and appropriate measurement is secured.

Also, with the present invention, because the parameters further include the magnitudes of the respective peak values of the first pulse, the second pulse, and the third pulse with respect to the prescribed criterial value, and when the magnitudes with respect to the prescribed criterial value of the respective peak values are P1, P2, and P3, respectively, the condition includes P1>P2 and P2<P3 in addition to the first condition or includes P1<P2 and P2>P3 in addition to the second condition, even when the detected pressure pulses are pulses that cannot be used in blood pressure calculation, a false positive, of treating the pressure pulses as pulse waves that can be used in blood pressure calculation due to the amplitudes and the intervals of the pulses meeting the first condition or the second condition due to drift of the pressure pulses, entry of noise, etc., can be prevented effectively.

What is claimed is:

1. A blood pressure measurement apparatus, operable to vary a pressure of a cuff wound around a portion of a living body to calculate a blood pressure value, the blood pressure measurement apparatus comprising:
   a pressure pulse detector, operable to continuously detect pressure pulses from a signal corresponding to the pressure of the cuff, the pressure pulses including a first pulse, a second pulse prior to the first pulse and a third pulse prior to the second pulse which are detected under the same pressure;
   a controller including a central processing unit configured to execute a blood pressure detecting program including the operations of
   determining a waveform amplitude of the first pulse (A1), a waveform amplitude of the second pulse (A2), a waveform amplitude of the third pulse (A3), an interval between the first pulse and the second pulse (T12) and an interval between the second pulse and the third pulse (T23);
   distinguishing whether or not the waveforms amplitudes of the first pulse and the second pulse are substantially identical with each other;
   distinguishing, when the waveform amplitudes are not substantially identical with each other, whether or not relationships between parameters of the first pulse, the second pulse and the third pulse meet a condition related to arrhythmia;
   determining the first pulse and the second pulse to be pulse waves when the waveform amplitudes are substantially identical with each other, and
   determining the first pulse, the second pulse and the third pulse to be pulse waves when the parameters meet the condition, and
   calculating the blood pressure value based on the pulse waves determined by the controller.

2. The blood pressure measurement apparatus according to claim 1, wherein a condition related to arrhythmia includes one or more states of (i) A1>A2, (ii) A2<A3, (iii) and T12>T23, (iv) A1<A2, (v) A2>A3 and (vi) T12<T23.

3. The blood pressure measurement apparatus according to claim 1, wherein the operations further include claim 2:
   determining a magnitude of a peak value of the first pulse with respect to a criterial value (P1); a magnitude of a peak value of the second pulse with respect to the criterial value (P2); and a magnitude of a peak value of the third pulse with respect to the criterial value (P3), and
   determining whether a condition related to arrhythmia exists when one or more of (i) P1 is larger than the P2 and the P2 is smaller than the P3 and (ii) the P1 is smaller than the P2 and the P2 is larger than the P3.

* * * * *